(12) United States Patent
Farah et al.

(10) Patent No.: US 6,312,704 B1
(45) Date of Patent: Nov. 6, 2001

(54) ORALLY ADMINISTRABLE COMPOSITION CAPABLE OF PROVIDING ENHANCED BIOAVAILABILITY WHEN INGESTED

(75) Inventors: Nabil Farah, Lyon; Joel Denis, Charley, both of (FR)

(73) Assignee: Gattefosse, S.A., Saint-Priest Cedex (FR)

( * ) Notice: Subject to any disclaimer, the term of this patent is extended or adjusted under 35 U.S.C. 154(b) by 0 days.

(21) Appl. No.: 09/487,391

(22) Filed: Jan. 18, 2000

Related U.S. Application Data

(63) Continuation-in-part of application No. 08/838,893, filed on Apr. 11, 1997, now Pat. No. 6,054,136, which is a continuation of application No. 08/433,489, filed on May 12, 1995, now abandoned.

(30) Foreign Application Priority Data

Sep. 30, 1993 (FR) ........................................................ 492177

(51) Int. Cl.⁷ .............................. A61K 6/00; A61K 7/00; A61K 9/64; A61K 9/48; A61K 9/20; A61K 13/00; A61K 9/70

(52) U.S. Cl. .......................... 424/401; 424/456; 424/451; 424/464; 424/443

(58) Field of Search ................................... 424/404, 443, 424/451, 456, 464

(56) References Cited

U.S. PATENT DOCUMENTS

| 4,719,239 | 1/1988 | Muller | 514/785 |
| 5,342,625 | 8/1994 | Hauer | 424/455 |

FOREIGN PATENT DOCUMENTS

| 0152945 | 9/1992 | (EP) . |
| 93/12766 | * 8/1993 | (WO) . |
| 93/23083 | 11/1993 | (WO) . |
| 94/14423 | * 7/1994 | (WO) . |
| 95/08983 | * 6/1995 | (WO) . |

* cited by examiner

Primary Examiner—Thurman K. Page
Assistant Examiner—Humera N. Shelkh
(74) Attorney, Agent, or Firm—Norris, McLaughlin & Marcus

(57) ABSTRACT

Composition for pharmaceutical or cosmetic use, capable of providing enhanced bioavailability when ingested, comprising at least a pharmaceutical active ingredient, a lipophilic phase consisting of a mixture of fatty acid esters and glycerides, a surfactant (SA), and a cosurfactant (CoSA). The lipophilic phase consists of a mixture of $C_8$ to $C_{18}$ polyglycolized glycerides having hydrophilic-lipophilic balance (HLB) of less than 16, this lipophilic phase representing from 32 to 75% of the total weight of the composition. The surfactant (SA) is chosen from the group comprising saturated $C_8$–$C_{10}$ polyglycolized glycerides and oleic esters of polyglycerol, this surfactant having an HLB of less than 16. The cosurfactant (CoSA) is chosen from the group comprising lauric esters of propylene glycol, oleic esters of polyglycerol and ethyl diglycol. The SA/CoSA ratio is between 0.5 and 6 and the hydrophilic phase of the final microemulsion is supplied after ingestion by the physiological fluid of the digestive milieu.

26 Claims, 2 Drawing Sheets

SA/CoSA = 1

SA/CoSA = 1

SA/CoSA = 0.5

Figure 1:
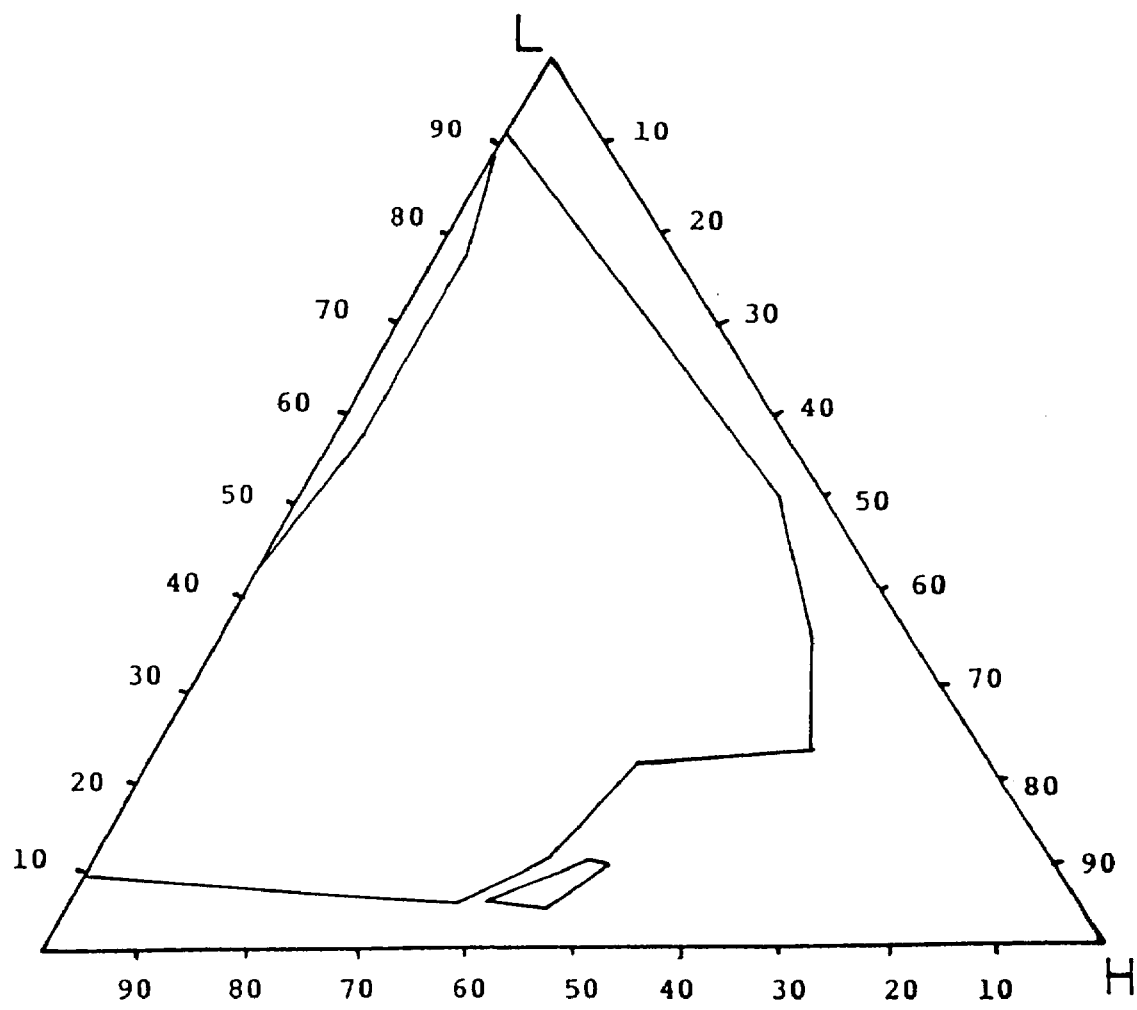

ORALLY ADMINISTRABLE COMPOSITION CAPABLE OF PROVIDING ENHANCED BIOAVAILABILITY WHEN INGESTED

CROSS-REFERENCE TO RELATED APPLICATIONS

This application is a continuation-in-part of Ser. No. 08/838,893, filed Apr. 11, 1997 now U.S. Pat. No. 6,054, 136, which in turn was a continuation of Ser. No. 08/433, 489, filed May 12, 1995 and now abandoned.

TECHNICAL FIELD

The invention relates to a composition which can be administered, in particular, orally, for pharmaceutical or cosmetic use, capable of forming a microemulsion in situ with the biological fluid of the body. The invention relates more especially to a composition composed of a self-microemulsifying carrier system for pharmaceutical active ingredients (also referred to herein as "agents"), designated in the art by the English term "SMEDDS" (self-microemulsifying drug delivery system). These systems have the property of microemulsifying in water at the temperature of the human body.

This composition is intended on the one hand to transport one or more soluble or sparingly soluble pharmaceutical active ingredients and on the other hand to form a microemulsion with the biological fluid of the human body, being understood that one or more pharmaceutical active ingredients or principles in solution in a microemulsion has better bioavailability.

PRIOR ART

As is known, a microemulsion is a fluid and stable homogeneous solution composed of four major constituents, respectively, a hydrophilic phase, a lipophilic phase, at least one surfactant (SA) and at least one cosurfactant (CoSA).

Microemulsions have been widely studied for oil recovery. There is hence no need to describe them here in detail.

A surfactant is a chemical compound possessing two groups, the first polar or ionic, which has a great affinity for water, the second which contains a longer or shorter aliphatic chain and is hydrophobic. These chemical compounds having marked hydrophilic character are intended to cause the formation of micelles in aqueous or oily solution.

A cosurfactant, also sometimes known as "co-surface-active agent", is also a chemical compound, but having hydrophobic character, intended to cause the mutual solubilization of the aqueous and oily phases in a microemulsion.

The invention is hence directed to increasing the bioavailability of pharmaceutical active ingredients which are difficult to dissolve, by solubilizing them within a microemulsion.

In the document EP-A-0,334,777, the Applicant has shown the possibility of using microemulsions in the pharmaceutical industry. In the document WO 93/12766, the Applicant has described particular compositions for pharmaceutical use, in the form of microemulsions intended to be packaged in the form of suppositories, in which the hydrophilic phase is supplied by the rectal fluid. This production gives excellent results for suppositories, but cannot meet the needs for compositions intended to be ingested orally, since the amount of biological fluid in the stomach or intestine is much larger than in the rectum (several deciliters). Now, the conditions of existence of microemulsions such as those described in the document WO 93/12766 necessitate a very small percentage of water (few milliliters).

In the document EP-A-0,152,294, a system of the type in question has been described, consisting of a lipophilic phase composed of oleic alcohol and/or of polar esters of $C_2$–$C_4$ alcohols with $C_8$–$C_{12}$ fatty acids, and, as surfactant, ethoxylated glycerol, the mixture containing from 35 to 85% by weight of water. These formulations contain appreciable proportions of water, thereby ruling out the form of presentation in hard gelatin capsules. On the other hand, the compositions containing water form a macroemulsion in situ and not a microemulsion, thereby greatly decreasing the bioavailability.

In the document WO 93/23083, published after the priority date of the present application, a system is described in which the anhydrous hydrophilic phase consists of a polyglycolized glyceride containing $C_8$–$C_{10}$ short chains. This system does not significantly improve the diffusion of pharmaceutical active agents through membranes. It does not enable hydrophilic pharmaceutical active agents to be transported, and does not permit the formation of an emulsion, still less of a microemulsion in situ, thereby not facilitating bioavailability.

The pharmaceutical and cosmetic industries are expressing an ever increasing demand for compositions free from an aqueous phase, in order to facilitate their packaging in the form of hard gelatin capsules, tablets and plasters. The compositions known at the present time for the manufacture of hard gelatin capsules, in particular the ones described In the above documents, are unable to meet the need, since the presence of water contained in these mixtures is incompatible with the technique employing hard gelatin capsules.

The invention solves these problems. It relates to an orally administrable composition, in particular for pharmaceutical or cosmetic use, comprising a lipophilic phase, at least one surfactant and at least one cosurfactant which, mixed and in the presence of physiological fluid, form a microemulsion facilitating dissolution in situ and improving the bioavailability of the pharmaceutical active ingredients.

DESCRIPTION OF THE INVENTION

This orally administrable composition capable of forming a microemulsion, comprising at least
  a pharmaceutical active ingredient,
  a lipophilic phase consisting of a mixture of fatty acid esters and glycerides,
  surfactant(SA),
  a cosurfactant (CoSA),
and is characterized
  in that the lipophilic phase consists of a mixture of $C_8$ to $C_{18}$ polyglycolized glycerides having a hydrophilic-lipophilic balance (HLB) of less than 16, this lipophilic phase representing from 1 to 75% of the total weight of the composition;
  the surfactant (SA) is chosen from the group comprising saturated $C_8$–$C_{10}$ polyglycolized glycerides and oleic esters of polyglycerol, this surfactant also having an HLB of less than 16;
  the cosurfactant (CoSA) has a different composition from the surfactant and consists of ethyl diglycol or a polyvalent alcohol selected from the group comprising lauric esters of propylene glycol, oleic esters of polyglycerol; and
  the SA/CoSA ratio is between 0.5 and 6.

The hydrophilic phase used to form the final microemulsion is supplied after ingestion by the physiological fluid of the digestive milieu.

In other words, the invention consists in having selected a particular lipophilic phase which, combined with specific surfactants and cosurfactants, forms a microemulsion in the presence of the physiological fluid of the stomach and intestine of the human or animal body. This composition improves the bioavailability of the pharmaceutical active ingredients within the body. The composition according to the invention can thus be administered effectively via the oral route.

Surprisingly, the use of lipophilic phase having considerable chain length enables the diffusion through membranes and the passage of pharmaceutical active ingredients or agents into the blood to be significantly improved.

In the description and in the claims:

"$C_8$–$C_{18}$ polyglycolized glycerides" denotes the lipophilic phase which is a reaction product consisting of a mixture of mono-, di- and triglycerides and polyethylene glycol (PEG) mono- and diesters, preferably of molecular weight between 200 and 4,000 and free glycerol and free PEG. The HLB value of the polyglycolized glycerides is adjusted by the length of the PEG chain and the melting point is adjusted by the length of the chains of the fatty acids, of the PEG and by the degree of saturation of the fatty chains. The HLB of the lipophilic phase is less than 16. The reactions employed to make the reaction product include partial alcoholysis of a starting oil consisting of a mixture of mono-, di- and triglycerides of fatty acids with PEG or esterification of glycerol and PEG with fatty acids or by mixing of glycerol esters and condensates of ethylene oxide with fatty acids, said fatty acids being selected from the group consisting of caprylic, capric, lauric, myristic, palmistic, stearic, oleic, linoleic and linolenic acids, at least 60% by weight in respect of total fatty acids containing 12 or more carbon atoms.

"$C_8$–$C_{10}$ polyglycolized glycerides" denotes the surfactant which is a reaction product consisting of a mixture of mono-, di- and triglycerides and polyethylene glycol (PEG) mono- and diesters, preferably of molecular weight between 200 and 400, free glycerol and free PEG. The HLB value of the polyglycolized glycerides is adjusted by the length of the PEG chain and the melting point is adjusted by the length of the chain of the fatty acids and the PEG. The HLB of surfactant is less than 16. The reactions employed to make the reaction product include partial alcoholysis of a fraction oil consisting of a mixture of triglycerides of fatty acids with PEG, esterification of glycerol and PEG with fatty acids or by mixing of glycerol esters and condensates of ethylene oxide with fatty acids, said fatty acids consisting of caprilic acid and capric acid.

Advantageously, in practice:

the polyglycolized glycerides of the lipophilic phase are saturated, thereby enabling mixtures which are solid at room temperature and liquid at human body temperature to be produced; this mixture has an HLB of less than 16, preferably between 9 and 15 and advantageously in the neighborhood of 14, of the type marketed by the Applicant under the registered trademark "GELUCIRE 44/14"; in effect, if the HLB value is greater than 16, the mixture becomes too hydrophilic, and this does not promote the microemulsion. It has been observed that best results are obtained when the HLB value is in the neighborhood of 14, since microemulsions can be formed over a widest range.

in a variant, a mixture of unsaturated $C_8$–$C_{18}$ polyglycolized glycerides, of HLB equal to 6 and which are liquid at room temperature, is used, such as the one marketed by the Applicant under the registered trademark "LABRAFIL WL 2609 BS";

the lipophilic phase represents from 1 to 75% of the weight of the composition, and preferably between 10 to 75% of the weight of the composition; it has been observed that, outside these limits, it is not possible to form a microemulsion which can be greatly diluted;

the surfactant (SA) is composed of $C_8$–$C_{10}$ polyglycolized glycerides, of HLB less than 16 and preferably between 5 and 14, such as the ones marketed by the Applicant under the registered trademarks "LABRAFAC CM 10", "LABRAFAC HYDROPHILE" or "LABRASOL", in a variant, the surfactant (SA) consists of oleic esters of polyglycerol, of HLB equal to 10, of the type marketed by the Applicant under the registered trademark "PLUROL OLEIQUE";

the cosurfactant (CoSA) is an ethyl diglycol, (also known as diethylene glycol monoethyl ether), such as the one marketed by the applicant under the registered trademark. "TRANSCUTOL";

in a variant, the cosurfactant (CoSA) consists of lauric esters of propylene glycol, of the type marketed by the Applicant under the registered trademark "LAUROGLYCOL";

in another variant, the cosurfactant (CoSA) consists of oleic esters of polyglycerol, of the type marketed by the Applicant under the registered trademark "PLUROL OLEIQUE", when it is not already used as a surfactant;

the SA/CoSA ratio is between 0.5 and 6, and preferably between 1 and 2; above 6 and below 0.5, the composition does not give a microemulsion which can be greatly diluted.

One of the main values of the invention is that, irrespective of the amount of water supplied by the gastric or intestinal physiological fluid of the human or animal body (of the order of a few deciliters), the mixture composed of this amount of water and the composition will form a microemulsion, enhancing the solubility of the active principle or agent, which increases the bioavailability in spite of the appreciable proportion of this physiological fluid.

It was hence necessary to determine the ranges of existence of the microemulsions in question. To this end, pseudoternary diagrams were plotted, keeping to a surfactant SA/cosurfactant CoSA ratio of 1. Mixtures of lipophilic phase +SA+CoSA were made in different proportions. To each of these mixtures, the hydrophilic phase was then added dropwise until a clear solution was obtained. This amount added corresponds to the minimum percentage of the hydrophilic phase needed to enter the microemulsified range. This is the so-called entry percentage. Addition of the hydrophilic phase then continues until cloudiness appears. The amount added then corresponds to the so-called exit percentage.

This method of construction of pseudoternary diagrams is called the "titration method". The region of existence of the microemulsion, to wit a clear and transparent solution, lies between two regions of existence of an emulsion, a dispersion having a milky appearance.

While, most generally, the initial composition intended to be ingested does not contain water, it is nevertheless useful for some uses for this composition to contain water, with the proviso, however, that the latter does not initially participate in the formation of the final microemulsion.

In effect, when the composition takes liquid form, consequently hygroscopic in nature, and is intended to be packaged in the form of hard gelatin capsules, the presence of small proportions of water can be useful to balance the uptake of water contained in the encapsulation envelope. It will be readily understood that this water does not participate in the formation of the final microemulsion, but quite simply permits the stability of the capsule and prevents it becoming brittle.

Figure 2:
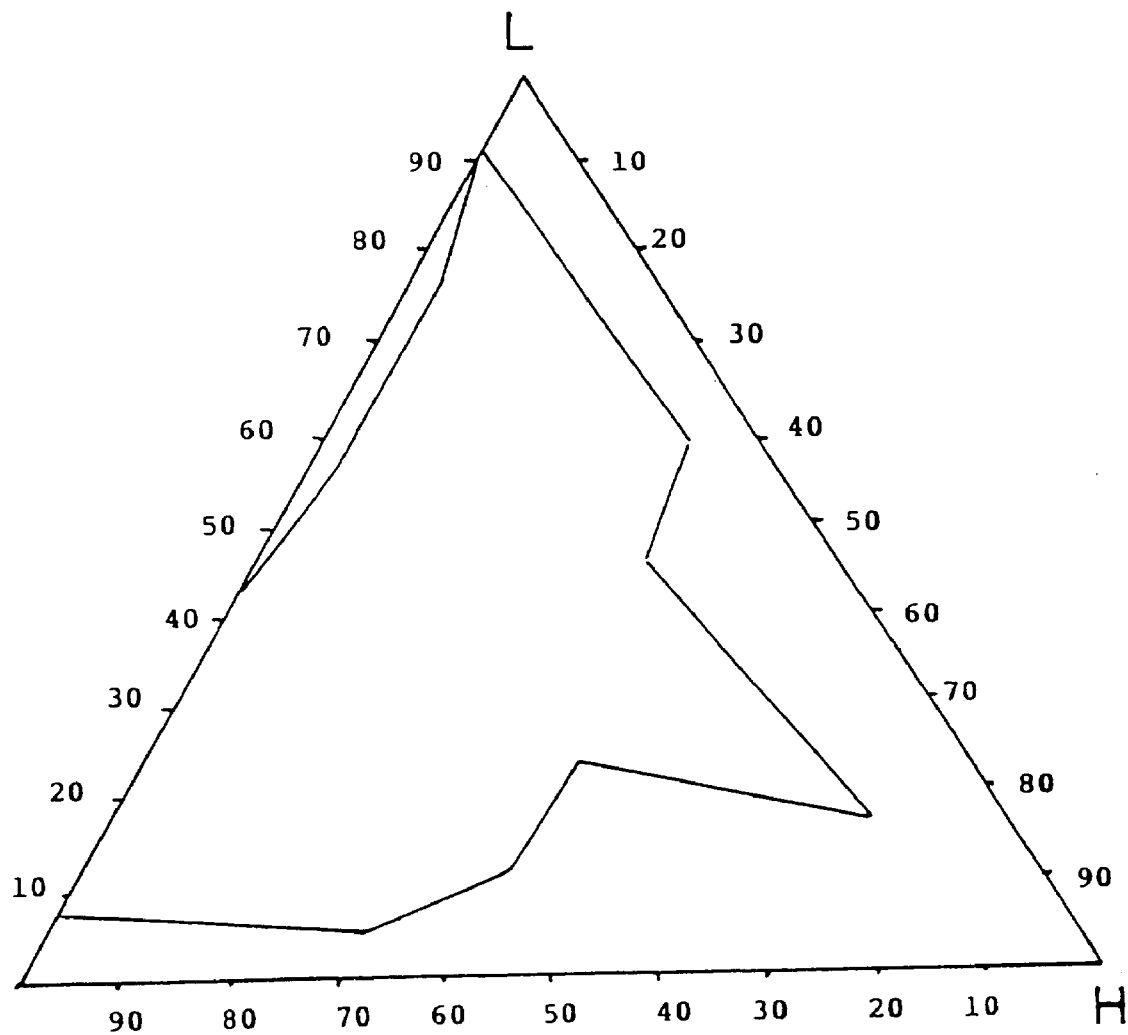

FIGS. 1 and 2 show pseudoternary diagrams of two preferred compositions of the invention.

In both cases, the surfactant (SA)-cosurfactant (CoSA) mixture is the same. Only the lipophilic phase differs. In both diagrams, it is clearly apparent that the range of existence of the microemulsion is very wide and corresponds to a high percentage of hydrophilic phase (from 0 to 60% in FIG. 1, from 0 to 70% in FIG. 2).

Consequently, the microemulsion will be able to form even within the digestive system, where the amount of biological fluid is large (of the order of a few deciliters).

The examples which follow bring out preferred compositions of the invention. It is self-evident that the percentage of active principles is dependent on the dosage of the active principle administered.

In all the examples, the complement by weight to 0% of the composition is, in actual fact, represented by an anti-inflammatory active principle, namely indomethacin in Examples 1 to 8, and 12, hydrocortisone in Example 9 and diclofenac sodium in Example 10. In examples 1–12, the hydrophilic phase is represented by water which is known to be a simulation of the digestive milieu for in vitro tests.

EMBODIMENTS OF THE INVENTION

Example 1

As lipophilic phase, a mixture of saturated $C_8$–$C_{18}$ polyglycolized glycerides having a melting point of 48° C. and an HLB of 9, marketed by the Applicant under the name "GELUCIRE 48/09", is used. This phase represents 73.7% of the total weight of the final composition.

The surfactant (SA)-cosurfactant (CoSA) mixture consists of a mixture of $C_8$–$C_{10}$ polyglycolized glycerides (SA), of HLB equal to 10, marketed by the Applicant under the name "LABRAFAC CM 10", and lauric esters of propylene glycol (CoSA) of the type marketed by the applicant under the name "LAUROGLYCOL". This mixture represents 18.5% of the weight of the composition, and the SA/CoSA ratio is equal to 0.5.

The composition obtained is solid at room temperature and becomes liquid at 37° C. It has many advantages compared to the traditional formulations used with the same pharmaceutical active agent. An excellent power of solubilization of the active agent in the digestive milieu and an excellent bioavailability may be noted, despite the fact that this active agent is lipophilic.

Tests of in vitro dissolution in a gastric medium at pH 1.2 showed that, with this formulation, a percentage of 48% of the active agent dissolved at the end of one hour is achieved. By way of comparison, when the pure active agent (indomethacin) is tested, at best only 5% of this active agent is dissolved in one hour; and still by way of comparison, with hard gelatin capsules of this active principle which are currently on the market, only 4.7% of active agent dissolved is obtained at the end of one hour.

It could not be foreseen that the composition according to the invention would enable the dissolution of the active agents to be improved to this extent (nearly tenfold).

Example 2

As lipophilic phase, a mixture of saturated $C_8$–$C_{18}$ polyglycolized glycerides having a melting point of 44° C. and an HLB of 14, marketed by the Applicant under the name "GELUCIRE 44/14", is used: this mixture represents 52.5% of the total weight of the final composition.

For the surfactant+cosurfactant mixture, the same components are used as in Example 1: this SA+CoSA mixture represents in this instance 35% of the weight of the composition, and the SA/CoSA ratio is equal to 0.5.

The same properties are observed as in Example 1.

Example 3

The same lipophilic phase is used, and in proportion, as in Example 2.

The surfactant+cosurfactant mixture consists of the same surfactant as in Examples 1 and 2, combined with a cosurfactant consisting of ethyl diglycol, marketed by the Applicant under the name "TRANSCUTOL" this SA+CoSA mixture represents 35% of the total weight of the final composition, and the SA/CoSA ratio is equal to 0.5.

Example 4

The same lipophilic phase is used as in Example 2. This lipophilic phase represents 73.7% of the total weight of the final composition.

The same SA+CoSA mixture is used as in Example 2; this mixture represents 18.5% of the weight of the final composition, and the SA/CoSA ratio is equal to 0.5.

Example 5

The same lipophilic phase is used, and in the same proportion, as in Example 2.

The surfactant+cosurfactant mixture consists of a mixture of oleic esters of polyglycerol, of HLB equal to 10, marketed by the Applicant under the name "PLUROL OLEIQUE" for the surfactant, the cosurfactant being the same as in Example 3, this mixture representing 35% of the weight of the composition, the SA/CoSA ratio being equal to 1.

This example is illustrated by the pseudoternary diagram of FIG. 1, in which the reference L denotes the lipophilic phase and the reference H the hydrophilic phase. The range of existence of the microemulsion is very wide, and corresponds to a high percentage of water (between 0 and 60%). In this way, the composition containing the active agents can be greatly diluted, thereby conferring on it a good solubilizing power in the digestive system and a good bioavailability of the active agents, something which could not be obtained hitherto.

Example 6

As lipophilic phase, a mixture of saturated $C_8$–$C_{18}$ polyglycolized glycerides having a melting point of 48° C. and an HLB of 12, marketed by the Applicant under the name "GELUCIRE 42/12", is used.

The same surfactant+cosurfactant system is used as in Example 1, and the lipophilic phase is replaced by a mixture of saturated $C_8$–$C_{18}$ is polyglycolized glycerides having a melting point of 42° C. and an HLB of 12.

This example is illustrated by the pseudotemary diagram of FIG. 2. The range of existence of the microemulsion is very wide, and corresponds to a high percentage of water (between 0 and 70%).

Example 7

As lipophilic phase, a mixture of saturated $C_8$–$C_{18}$ polyglycolized glycerides having a melting point of 44° C. and an HLB of 14, marketed by the Applicant under the name "GELUCIRE 44/14", is used. This phase represents 45.2% of the total weight of the final composition.

As surfactant SA, the same mixture is used as in Example 1, in a proportion of 3.7% of the total weight of the composition.

As cosurfactant, the same compound is used as in Example 5, named "PLUROL OLEIQUE", in this instance acting as cosurfactant, in the proportion of 7.5%.

The SA/CoSA ratio is equal to 1 and the pharmaceutical active agent (indomethacin) represents 43.5% of the total.

Example 8

In vivo tests were conducted on rats with indomethacin as active agent.

The proportions by weight of the different constituents of this mixture are:

| Surfactant: | LABRASOL | 44.90% |
|---|---|---|
| Cosurfactant | PLUROLOLEIQUE | 15.00% |
| Lipophilic phase: | LABRAFIL WL 2609 BS | 39.90% |
| Active agent: | Indomethacin | 0.20% |

An oral administration of indomethacin is first carried out according to the above composition. The results show that, after one hour, the plasma concentrations lie between 5 and 7 micrograms per milliliter (g/ml), and after two hours between 7 and 13 g/ml.

A second series of tests consists in administering indomethacin orally in the form of powder made into a suspension immediately before use. It is found that, after one hour, the plasma concentrations lie between 1 and 5 g/ml, and after two hours between 1 and 4 g/ml. The kinetics obtained are irregular and vary from one animal to another.

The bioavailability is approximately twice as large in the case of the administration according to the invention.

Example 9

In this example, the rates of dissolution of hydrocortisone in a gastric medium (at pH 1.2) are compared.

The same lipophilic phase and the same SA/CoSA mixture are used as in Example 8, but in the following proportions:

| Hydrocortisone | 4.0% |
|---|---|
| Lipophilic phase | 19.2% |
| Surfactant | 57.6% |
| Cosurfactant | 19.2% |

In this way, it is possible to obtain a rate of dissolution in vitro ranging up to 50% in 45 minutes (min), whereas hydrocortisone in powder form displays a dissolution of 10% in 45 min.

Example 10

In this example, the rates of dissolution in vitro in a gastric medium (at pH 1.2), in which diclofenac sodium in powder form is almost insoluble, are compared.

The proportions by weight of the different constituents of this mixture are:

| Surfactant: | LABRASOL | 38.40% |
|---|---|---|
| Cosurfactant: | PLUROLOLEIQUE | 38.40% |
| Lipophilic phase: | LABRAFIL 2609 BS | 19.20% |
| Active agent: | diclofenac sodium | 4.00% |

In this way, it is possible to obtain a rate of dissolution ranging up to 86% in 30 min, whereas diclofenac sodium in powder form has a rate of dissolution of 1% in the same time.

Example 11

In this example, the rates of dissolution in vitro in a gastric medium (at pH =1.2), in which indomethacin alone has a rate of dissolution of less than 5% in the same medium, are compared.

The proportions by weight of the different constituents of this mixture are:

| Surfactant: | LABRASOL | 57.60% |
|---|---|---|
| Cosurfactant: | PLUROLOLEIQUE | 19.20% |
| Lipophilic phase: | LABRAFIL WL 2609 BS | 19.20% |
| Active agent: | Indomethacin | 4.00% |

Example 12

In this example, the same components are used as in the preceding example, with different proportions, namely:

| Surfactant: | LABRASOL | 43.40% |
|---|---|---|
| Cosurfactant: | PLUROLOLEIQUE | 14.40% |
| Lipophilic phase: | LABRAFIL WL 2609 BS | 38.40% |
| Active agent: | Indomethacin | 4.00% |

A rate of dissolution of 90% in 30 min is obtained. It is observed that an increase in the lipophilic phase improves the dissolution to a significant degree.

Example 13

The purpose of this example is to investigate the relative bioavailability of 2-indomethacin formulations (DH 0202 and DH 0203) of the invention at different concentrations versus a reference indomethacin formulation in aqueous suspension at a concentration of 2 mg/ml in male Sprague Dawley rats. The proportion by weight of the different constituents of formulations are represented in the following table.

|  | DH 0202 | DH 0203 |
|---|---|---|
| LABRASOL ® (Surfactant) | 77.15 | 8.33 |
| LAUROGLYCOL ® FFC (Cosurfactant) | 12.85 | 16.67 |
| GELUCIRE ® 44/14 (Lipophilic phase) | 9.80 | 74.80 |
| RATIO (Surfactant/Cosurfactant) | R = 6 | R = 0.5 |
| INDOMETHACIN | 0.20 | 0.20 |
| TOTAL | 100.00 | 100.00 |

Three groups of 30 rats each were treated orally with the three formulations. In each group, 3 per time were sacrificed and plasma collected at the following times after dosing: 0.25–0.5–1–1.5–2–4–6–8–24 and 48 hours.

The plasma concentrations of indomethacin were evaluated according to an HPLC-UV method (hight-performance liquid chromatography with ultra-violet detection, Journal of Chromatography B.692, 1997, 241–244).

Indomethacin was absorbed after the reference formulation administration and peaked at 4 hours, with a $C_{max}$ of 14,409 ng/ml. Indomethacin was eliminated with an elimination half life of 4.4 hours. The AUC (Area under the plasma concentration versus time curve) was 119,174 h*ng/ml.

An increase of AUC was observed and was statistically significant for both indomethacin formulations of the invention versus the reference formulation.

The highest increase of bioavailability (37%) was observed with formulation DH 0202, F=1.37.

Formulation DH 0203 shows an increase of bioavailability of 29% (F=1.29).

The compositions according to the invention have many advantages compared to the ones which are already known. The absence of an aqueous phase, which facilitates packaging of these pharmaceutical compositions, especially in the form of hard gelatin capsules, soft capsules, tablets or plasters, may be mentioned.

Thus, the invention may hence be administered orally.

It hence proves to be the case that the invention enables the choice both of the packaging and of the administration of compositions for pharmaceutical or cosmetic use to be broadened. Consequently, the industrial exploitation of the compositions according to the invention will be facilitated and may be contemplated successfully.

What is claimed is:

1. A pharmaceutical composition for oral administration, providing enhanced bioavailability when ingested and contacted with biological fluids of the body, comprising a lipophilic phase, a surfactant, a cosurfactant and a pharmaceutical active ingredient;

the lipophilic phase being present in an amount of from 1 to 75% by weight based on the total weight of the composition; the surfactant, cosurfactant and pharmaceutical active ingredient comprising the remainder and the ratio of surfactant to cosurfactant being between 0.5 and 6;

the lipophilic phase having a hydrophilic-lipophilic balance (HLB) of less than 16 and being obtained by esterification of polyethylene glycol and glycerol with fatty acids, or by mixing of glycerol esters and condensates of ethylene oxide with fatty acids, said fatty acids being selected from the group consisting of caprylic, capric, lauric, myristic, palmitic, stearic, oleic, linoleic and linolenic acids, at least 60% by weight in respect of total fatty acids containing 12 and more carbon atoms;

the surfactant having an HLB of less than 16 and selected from the group consisting of oleic esters of polyglycerol or a product obtained by esterification of glycerol and polyethylene glycol with caprylic acid and capric acid, or by mixing of glycerol esters and condensates of ethylene oxide with caprylic acid and capric acid; and the cosurfactant having a different composition from the surfactant and consisting of ethyl diglycol or a polyvalent alcohol ester selected from the group consisting of lauric esters of propylene glycol and oleic esters of polyglycerol, and where each of said lipophilic phase, surfactant, cosurfactant and pharmaceutical active ingredient are miscible and substantially anhydrous; said composition providing enhanced bioavailability when ingested and contacted with the biological fluids of the body.

2. The composition of claim 1 wherein the reaction product of the lipophilic phase is saturated to provide a composition which is solid at room temperature.

3. The composition of claim 1 wherein the reaction product of the lipophilic phase is unsaturated to provide a composition which is liquid at room temperature.

4. The composition of claim 1 wherein the lipophilic phase has an HLB of about 14.

5. The composition of claim 3 wherein the lipophilic phase has an HLB equal to 6 and is liquid at room temperature.

6. The composition of claim 1 wherein the lipophilic phase is from 50 to 75% of the weight of the composition.

7. The composition of claim 1 wherein the surfactant consists of oleic esters of polyglycerol having an HLB equal to 10.

8. The composition of claim 1 wherein the ratio of surfactant to cosurfactant is between 1 and 2.

9. A method of increasing the bioavailability of a pharmaceutical active ingredient which is difficult to dissolve, said method comprising:

providing a pharmaceutical composition for oral administration, said composition comprising a lipophilic phase, a surfactant, a cosurfactant and a pharmaceutical active ingredient;

the lipophilic phase being present in an amount of from 1 to 75% by weight based on the total weight of the composition; the surfactant, cosurfactant and pharmaceutical active ingredient comprising the remainder and the ratio of surfactant to cosurfactant being between 0.5 and 6;

the lipophilic phase having a hydrophilic-lipophilic balance (HLB) of less than 16 and being obtained by esterification of glycerol and polyethylene glycol with fatty acids or by mixing of glycerol esters and condensates of ethylene oxide with fatty acids, said fatty acids being selected from the group consisting of caprylic, capric, lauric, myristic, palmitic, stearic, oleic, linoleic and linolenic acids, at least 60% by weight in respect of total fatty acids containing 12 and more carbon atoms;

the surfactant having an HLB of less than 16 and selected from the group consisting of oleic esters of polyglycerol or obtained by esterification of glycerol and polyethylene glycol with caprylic acid and capric acid, or by mixing of glycerol esters and condensates of ethylene oxide with caprylic and capric acid; and the cosurfactant having a different composition from the surfactant and consisting of ethyl diglycol or a polyvalent alcohol ester selected from the group consisting of lauric esters of propylene glycol and oleic esters of polyglycerol, and where each of said lipophilic phase, surfactant, cosurfactant and pharmaceutical active ingredient are miscible and substantially anhydrous; said composition providing enhanced bioavailability when ingested and contacted with the biological fluids of the body; and ingesting said composition whereby said composition contacts the biological fluids of the body and increases the bioavailability of the pharmaceutical active ingredient.

10. The method of claim 9 wherein the reaction product of the lipophilic phase is saturated to provide a composition which is solid at room temperature.

11. The method of claim 9 wherein the reaction product of the lipophilic phase is unsaturated to provide a composition which is liquid at room temperature.

12. The method of claim 9 wherein the lipophilic phase is from 50 to 75% of the weight of the composition.

13. The method of claim 9 wherein the ratio of surfactant to cosurfactant is between 1 and 2.

14. A method of administering a pharmaceutical active ingredient to a host such that the bioavailability of the pharmaceutical active ingredient is increased, said method comprising the steps of:

providing a pharmaceutical composition for oral administration, said composition comprising a lipophilic phase, a surfactant, a cosurfactant and a pharmaceutical active ingredient;

the lipophilic phase being present in an amount of from 1 to 75% by weight based on the total weight of the composition; the surfactant, cosurfactant and pharmaceutical active ingredient comprising the remainder and the ratio of surfactant to cosurfactant being between 0.5 and 6;

the lipophilic phase having a hydrophilic-lipophilic balance (HLB) of less than 16 and being obtained by esterification of glycerol and polyethylene glycol with fatty acids or by mixing of glycerol esters and condensates of ethylene oxide with fatty acids, said fatty acids being selected from the group consisting of caprylic, capric, lauric, myristic, palmitic, stearic, oleic, linoleic and linolenic acids, at least 60% by weight in respect of total fatty acids containing 12 and more carbon atoms;

the surfactant having an HLB of less than 16 and selected from the group consisting of oleic esters of polyglycerol or a product obtained by esterification of glycerol and polyethylene glycol with caprylic acid and capric acid, or by mixing of glycerol esters and condensates of ethylene oxide with caprylic and capric acid; and the cosurfactant having a different composition from the surfactant and consisting of ethyl diglycol or a polyvalent alcohol ester selected from the group consisting of lauric esters of propylene glycol and oleic esters of polyglycerol, and where each of said lipophilic phase, surfactant, cosurfactant and pharmaceutical active ingredient are miscible and substantially anhydrous; said composition providing enhanced bioavailability when ingested and contacted with the biological fluids of the body; and administering said composition to said host for ingestion, whereby said composition contacts the biological fluids of the body and increases the bioavailability of the pharmaceutical active ingredient.

15. The method of claim 14 wherein the reaction product of the lipophilic phase is saturated to provide a composition which is solid at room temperature.

16. The method of claim 14 wherein the reaction product of the lipophilic phase is unsaturated to provide a composition which is liquid at room temperature.

17. The method of claim 14 wherein the lipophilic phase is from 50 to 75% of the weight of the composition.

18. The method of claim 14 wherein the ratio of surfactant to cosurfactant is between 1 and 2.

19. A method of making pharmaceutical composition for oral administration, providing enhanced bioavailability when ingested and contacted with biological fluids of the body, comprising admixing a lipophilic ingredient capable of forming a lipophilic phase with a surfactant, a cosurfactant and a pharmaceutical active ingredient;

the lipophilic phase being present in an amount of from 1 to 75% by weight based on the total weight of the composition; the surfactant, cosurfactant and pharmaceutical active ingredient comprising the remainder and the ratio of surfactant to cosurfactant being between 0.5 and 6;

the lipophilic phase having a hydrophilic-lipophilic balance (HLB) of less than 16 and being obtained by esterification of polyethylene glycol and glycerol with fatty acids, or by mixing of glycerol esters and condensates of ethylene oxide with fatty acids, said fatty acids being selected from the group consisting of caprylic, capric, lauric, myristic, palmitic, stearic, oleic, linoleic and linolenic acids, at least 60% by weight in respect of total fatty acids containing 12 and more carbon atoms;

the surfactant having an HLB of less than 16 and selected from the group consisting of oleic esters of polyglycerol or a product obtained by esterification of glycerol and polyethylene glycol with caprylic acid and capric acid, or by mixing of glycerol esters and condensates of ethylene oxide with caprylic acid and capric acid; and the cosurfactant having a different composition from the surfactant and consisting of ethyl diglycol or a polyvalent alcohol ester selected from the group consisting of lauric esters of propylene glycol and oleic esters of polyglycerol, and where each of said lipophilic phase, surfactant, cosurfactant and pharmaceutical active ingredient are miscible and substantially anhydrous; said composition providing enhanced bioavailability when ingested and contacted with the biological fluids of the body.

20. The method of claim 19 wherein the reaction product of the lipophilic phase is saturated to provide a composition which is solid at room temperature.

21. The method of claim 19 wherein the reaction product of the lipophilic phase is unsaturated to provide a composition which is liquid at room temperature.

22. The method of claim 19 wherein the lipophilic phase has an HLB of about 14.

23. The method of claim 19 wherein the lipophilic phase has an HLB equal to 6 and is liquid at room temperature.

24. The method of claim 19 wherein the lipophilic phase is from 50 to 75% of the weight of the composition.

25. The method of claim 19 wherein the surfactant consists of oleic esters of polyglycerol having an HLB equal to 10.

26. The method of claim 19 wherein the ratio of surfactant to cosurfactant is between 1 and 2.

* * * * *